(12) United States Patent
Keitel et al.

(10) Patent No.: US 7,098,956 B2
(45) Date of Patent: Aug. 29, 2006

(54) PROCESS AND DEVICE FOR THE VIDEO RECORDING OF AN ILLUMINATED FIELD

(75) Inventors: Joachim Keitel, Bruchköbel (DE); Uwe Gampe, Duisburg (DE); Jörg Eduard Hartge, Gelnhausen (DE); Matthias Helten, Söhrewald (DE); Rudolf Marka, Frankfurt (DE)

(73) Assignee: Heraeus Med GmbH, Hanau (DE)

( * ) Notice: Subject to any disclaimer, the term of this patent is extended or adjusted under 35 U.S.C. 154(b) by 740 days.

(21) Appl. No.: 10/017,164

(22) Filed: Dec. 14, 2001

(65) Prior Publication Data

US 2002/0080237 A1    Jun. 27, 2002

(30) Foreign Application Priority Data

Dec. 19, 2000    (DE) ................ 100 63 380

(51) Int. Cl.
*H04N 5/222*    (2006.01)

(52) U.S. Cl. ............ 348/370; 348/131; 348/143; 348/373; 348/375; 348/208.14; 348/169; 348/170; 348/171; 348/172

(58) Field of Classification Search ............... 348/68, 348/131, 139, 143, 155, 157, 370, 371, 373, 348/374, 375, 208.14, 169–172
See application file for complete search history.

(56) References Cited

U.S. PATENT DOCUMENTS

| | | | |
|---|---|---|---|
| 4,081,214 A * | 3/1978 | Van Buskirk | 356/3.03 |
| 4,639,838 A | 1/1987 | Kato et al. | |
| 4,881,128 A | 11/1989 | Yamada | |
| 5,347,431 A * | 9/1994 | Blackwell et al. | 362/11 |
| 5,373,319 A * | 12/1994 | Lee | 348/143 |
| 5,457,325 A * | 10/1995 | Huberty | 250/559.29 |
| 5,808,680 A | 9/1998 | Steckhan | |
| 6,441,888 B1 * | 8/2002 | Azuma et al. | 356/4.01 |
| 6,483,536 B1 * | 11/2002 | Aoyama | 348/139 |
| 6,498,564 B1 * | 12/2002 | Oda | 340/567 |
| 6,762,794 B1 * | 7/2004 | Ogino | 348/262 |
| 6,878,924 B1 * | 4/2005 | Baron | 250/221 |
| 6,891,978 B1 * | 5/2005 | Takano | 382/284 |

* cited by examiner

*Primary Examiner*—David Ometz
*Assistant Examiner*—Chriss Yoder
(74) *Attorney, Agent, or Firm*—Klaus P. Stoffel; Wolff & Samsom PC

(57) ABSTRACT

For the video recording of a field illuminated by a lamp, especially a surgical lamp, where at least one light beam for illuminating the field emerges from a light exit area of a lamp housing in the direction of a predetermined housing axis, the optical axis of a video camera mounted with freedom to swivel a certain distance away from the exit point of the light beam is shifted automatically by a positioning element until the axis at least approximately intersects the light beam in the area of the illuminated field. The positioning element is driven by signals from a control unit. The video camera is preferably shifted in a stepwise manner. The distance to the illuminated field is determined by the fine focusing of the camera by the autofocus function, and then signals are transmitted from the control unit to the positioning element of the camera to compensate for the parallax between the optical axis of the camera and the light beam or beams emerging from the lamp.

9 Claims, 2 Drawing Sheets

PROCESS AND DEVICE FOR THE VIDEO RECORDING OF AN ILLUMINATED FIELD

BACKGROUND OF THE INVENTION

The invention pertains to a process for the video recording of field illuminated by a lamp, especially a surgical lamp, where at least one light beam for illuminating the field emerges in the direction of a predetermined housing axis from at least one light exit area of a lamp housing. The invention also pertains to a corresponding device.

A process for transmitting video signals and an image transmission system for surgical lamps is known from DE 195-23,377 C1. For this purpose, a surgical lamp is equipped with a video camera near the lamp housing to produce external images of the surgical field in association with a monitor screen and a control device. An adjustable suspension device is used to connect the lamp housing to a hanger bracket on the ceiling of the operating room.

FIG. 1 of this DE reference shows a lamp in which the video camera is mounted off-center.

The problem with a setup such as this is that any adjustment of the surgical lamp relative to the object being recorded, i.e., the surgical field, also results in a change in the orientation of the image with respect to the surgical field, i.e., a change in the appearance of the field being shown. As a result, it is possible that the image being reproduced will be appear to the surgeon to be displaced or rotated with respect to the original view of the surgical field.

An image transmission system for a video camera in conjunction with a surgical lamp and a control device with a monitor screen and a control unit is also known from EP 0,989,744 A1, which system has at least one image sensor in the camera, which is mounted in an adjustable support, where the control unit actuates at least one drive device to position at least the image sensor relative to the object being recorded. The video camera in this case is connected to the body of a surgical lamp, which is held in a stationary mount by means of an adjustable suspension. At least the image sensor of the video camera is supported with freedom to rotate around its optical axis, and the video camera is mounted in a swivel bearing located in the body of the surgical lamp, the axis of the swivel bearing extending approximately perpendicular parallel to the optical axis of the video camera.

The problem here is that only a frontal view in the direction in which the object being recorded is illuminated is possible.

When the camera, especially a video camera, is to be attached to a lamp, such as a surgical lamp, it can be necessary or desirable to mount the camera outside the optical axis of this lamp. In this case, the optical axis of the camera must be at an angle to the optical axis of the lamp so that it can illuminate the center of the field. We speak in this case of a parallax between the two objects.

SUMMARY OF THE INVENTION

The task of the invention is to correct the parallax associated with a shift in the position of the lamp with respect to the illuminated object in such a way that the optical axis of the camera or video camera is redirected to aim at the center of the illuminated field again after the lamp has been shifted.

The task is accomplished according to the process of the invention in that the optical axis of the video camera, which is set up in an adjustable or swivelable manner a certain distance away from the point where the light beam exits the lamp, is shifted automatically by means of a positioning element until it intersects the minimum of one light beam in the area of the illuminated field.

It has been found advantageous to have the ability to view the illuminated object from different perspectives, so that even remote observers can obtain an accurate image or derive a 3-dimensional impression of the object on the associated monitor.

The positioning element is preferably driven by signals from a control unit.

In a preferred embodiment of the process, the video camera is shifted in stepwise manner relative to the given axis of the lamp housing until the optical axis of the camera at least approximately intersects the light beam or the given (housing) axis.

The video camera is preferably shifted in a stepwise manner. The distance to the illuminated field is determined by sharpening the focus with the help of the autofocus function of the video camera, and then signals are sent from the control unit to the camera positioning element to compensate for the parallax between the optical axis of the camera and the light beam or beams.

It has been found advantageous for the image to be enlarged before the fine adjustment of the focus. For this purpose, before the fine-focusing function is activated, i.e., before the autofocus function of the camera is activated, for example, the focal length of the zoom lens is increased to the maximum ("TV" setting). After the image has been fine-focused, the focal length is set back again to the original value.

It is advantageous for the orientation of the optical axis of the camera to be corrected in an iterative manner.

The process is carried out by a lamp, especially a surgical lamp, with at least one lamp housing, from which at least one light beam for illuminating an illuminated field exits in the direction of a predetermined axis. The lamp housing has at least one video camera, which is set up a certain distance away from the exit area of the light beam or beams or from the predetermined axis. The optical axis of the video camera can be shifted automatically with respect to the minimum of one light beam or the predetermined axis by a positioning element in response to positioning signals from a control unit until the optical axis of the camera intersects the illuminated field.

It has been found advantageous for the camera to pan rapidly, which takes place almost automatically.

In a preferred embodiment of the lamp, a control unit or tracking controller is provided to drive the video camera positioning element. The unit or controller receives driving signals, which depend on the orientation of the predetermined axis of the lamp housing and the distance to the illuminated field, measured from the camera.

It is advantageous for the distance to the illuminated field to be corrected in an iterative manner, where the information on the orientation of the camera sent to the control unit is based on the number of completed adjusting steps, and where the information on the distance to the illuminated field is provided by the autofocus function. From this information, it is easy to determine the distance between the lamp housing and the illuminated field on the basis of a trigonometric conversion, inasmuch as the distance between the axis of the lamp housing and the video camera always remains the same.

An angle sensor, which detects the orientation of the optical axis of the camera in space, can also be used to generate the various driving signals.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PREFERRED EMBODIMENTS

Figure 1:
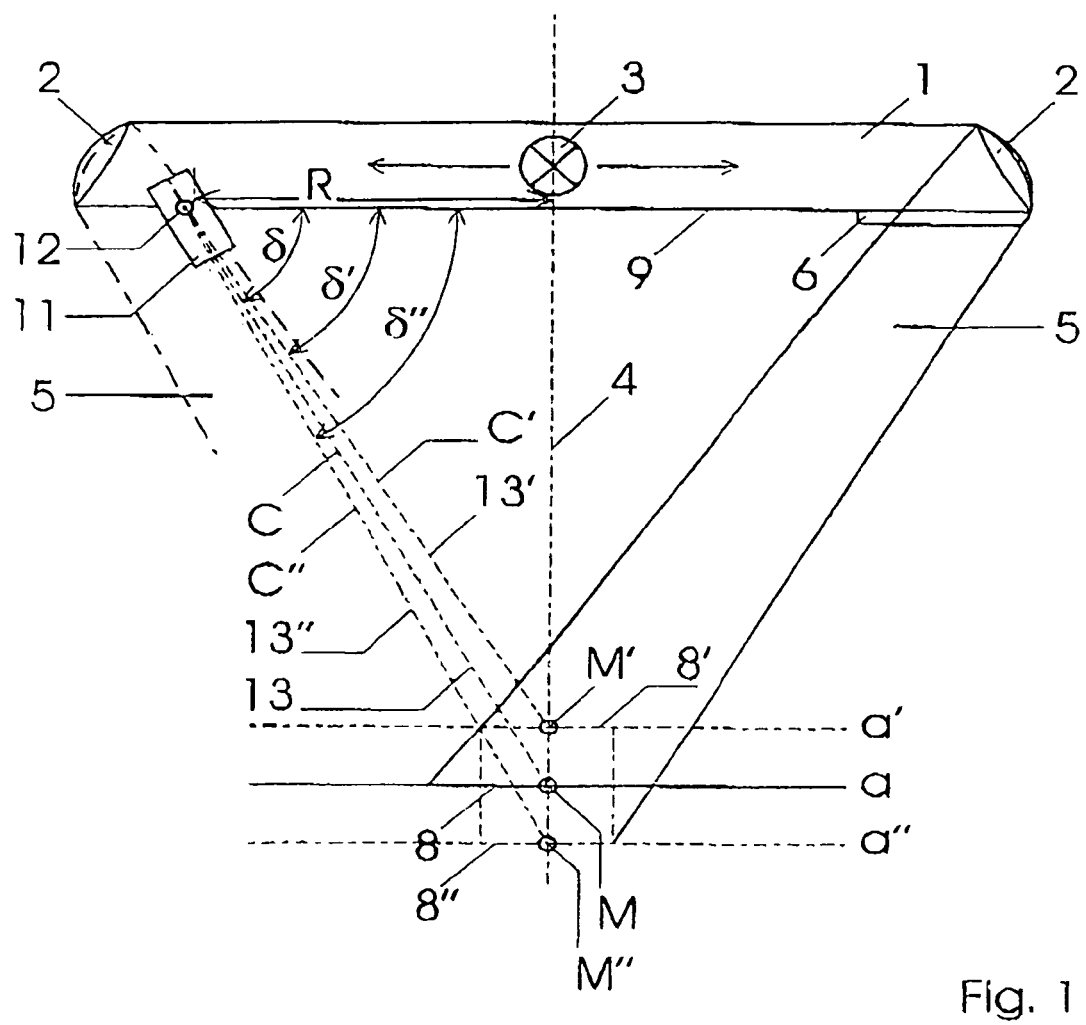
FIG. 1 is a longitudinal section through a surgical lamp according to the invention, where the lamp and the path of the beam are illustrated schematically.

According to FIG. 1, the lamp housing 1 of the surgical lamp has a ring-shaped reflector 2, shown here schematically, which is illuminated by at least one centrally located light source 3—on a longitudinal axis 4—in the position indicated schematically. The ring-shaped reflector 2 is designed so that an axially symmetric or concentric light beam 5 (only part of which is shown for the sake of clarity), extending along the longitudinal axis 4, is formed, which ensures that the field 8 will be illuminated without cast shadows. As a result, any objects which may be projecting into the light beam 5 such as the surgeon's instruments, the surgeon's hands or head, etc., will not cast any shadows, and thus the surgical field will remain well-lit at all times.

On the bottom 9 of the lamp housing 1, i.e., the side facing the illuminated field 8, a video camera 11 is placed off-center with respect to the longitudinal axis 4 and a certain distance away from the light source 3. This camera 11 makes it possible for an observer to obtain a perspective view of the surgical field, such as a wound, on a display screen. The video camera 11 is mounted by suitable joints on a bracket 12, so that its optical axis 13, i.e., the pivoting angle of the camera 11 (angle between the optical axis 13 and a plane or light exit surface perpendicular to the axis 4) can be adjusted by means of a positioning element (not shown here) in such a way that the optical axis 13 is directed at the center point M of the illuminated field 8 and thus intersects at least approximately the longitudinal axis 4 within a small encompassing circle. As soon as the distance a between the lamp housing 1 or the light exit surface 6 and the illuminated field 8 is decreased from a to a', the optical axis 13 of the camera must converge more sharply if it is to continue to aim directly at the new center M' of the illuminated field 8'. The realignment of the optical axis associated with the decrease to distance a' is designated 13'.

Because the distance C between the camera 11 and the illuminated field 8' has now been decreased to a value C', it is possible, on the basis of a trigonometric calculation ($\cos \delta = R/C$, $\cos \delta' = R/C'$) to determine the angle $\delta'$ by means of the arc function, from which the distance a ($a = c \cdot \sin \delta$, $a' = c' \cdot \sin \delta'$) can also be obtained.

On the basis of the new calculated angle $\delta'$, the camera 11 is swiveled in steps by means of a control unit (not shown here) and a drive motor acting as a positioning element until the value calculated for $\delta'$ is reached.

Conversely, when the distance between the light exit surface 6 of the lamp housing 1 shown here schematically and the illuminated field 8'' is increased to a'' a wider angle of the optical axis 13'' is set, so that the video camera 11 can continue to supply an image of the center of the illuminated field 8'' The corresponding trigonometric equations are in this case:

$$\cos \delta'' = R/C'' \text{ and } a'' = c'' \cdot \sin \delta''$$

Figure 2:
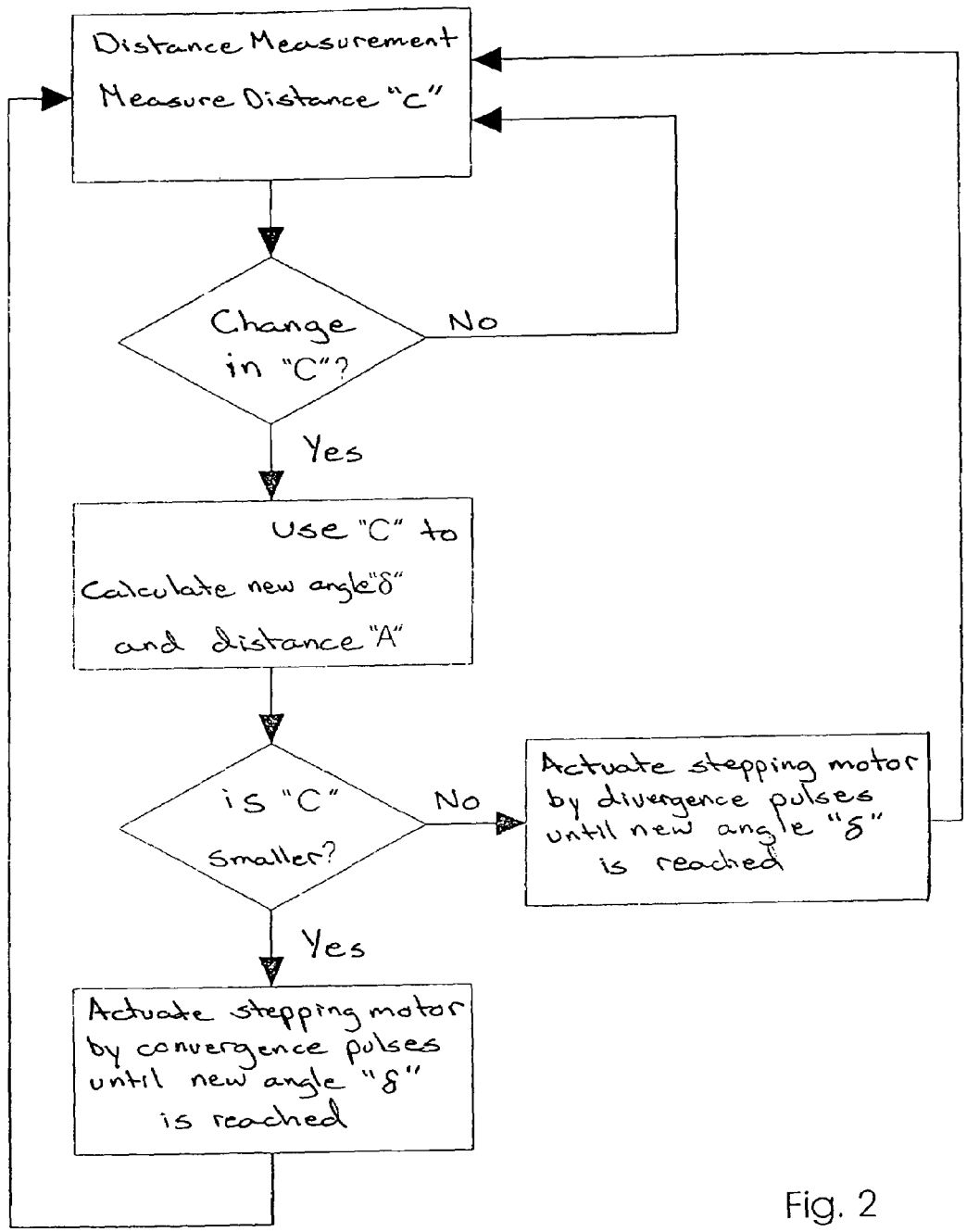
FIG. 2 is a functional block diagram in the form of a flow diagram to illustrate the sequence of operations by which the optical axis of the video camera is controlled.

With the help of a control unit (digital processing unit, not shown here for the sake of clarity), the parallax is corrected in steps as follows in a first embodiment according to FIG. 2:

1. Measure the distance.
2. Set the angle in correspondence with the distance.
3. Measure the distance.
4. If result 1 is not equal to result 3, go back to 1.

In principle, it can be assumed that this method is stable even in unfavorable cases after a few (no more than four or five) steps. To detect errors, the control unit is programmed so that, when the process does not stabilize, the angle is set to a standard distance (in the case of surgical lamps, this distance is one meter).

With the help of the control unit, furthermore, the parallax is corrected in steps as follows in a second embodiment:

1. Measure the intensity of illumination.
2. Tilt the camera one step outwardly.
3. Measure the intensity of illumination.
4. If result 3 is larger than result 1, go back to 1; otherwise, continue with 5.
5. Measure the intensity of illumination.
6. Tilt camera one step inwardly.
7. Measure the intensity of illumination.
8. If result 7 is larger than result 5, go back to 5.

In this embodiment, preferably the brightness signal provided in any case by a video camera (for surgical lamps) as part of the automatic illumination setting function is used to determine the intensity of illumination.

As an alternative, the intensity of illumination can also be determined by means of a light meter installed in or on the video camera.

It has been found to be especially advantageous for the sensor or sensors and the adjusting elements to be in the video camera 11 or to be connected to its bracket 12, so that a compact regulation or control system can be obtained under good hygienic conditions.

With the help of the autofocus function built into the camera 11, the distance between the illuminated field 8 and the camera 11 is determined, and then a correction is made for the parallax to the extent that parallax compensation can be accomplished on the basis of the known distance between the camera and the illuminated plane. This is accomplished preferably in an iterative manner, as will be explained below on the basis of an example:

In its original task position, the lamp is 1.3 m away from the wound, for example, and then it is lowered to a distance of, for example, 0.8 m. The parallax setting must then be recalculated and reset. In practice, it often happens that, when the lamp body is moved, it assumes a new angle to the operating table. In this case, the distance which the camera measures under the original parallax, which is correct for 1.3 m will not be correct for the new axis of the lamp, because, as a result of the slanted position of the lamp, the distance between the peripheral part of the lamp body (that is, the area farther toward the outside) and the wound is different than that in the middle of the lamp. After the first parallax correction, the camera is therefore positioned closer to the axis of the lamp, but it is still not in the completely correct position. In addition, the image will be rather out-of-focus, because the fine focusing was, after all, done before the lamp was tilted.

For this reason, when the lamp is not aimed directly at the object to be recorded, the parallax correction must be repeated several times until both the distance measurement and the angle adjustment are stable. This means that, first, when the lamp housing 1 is shifted, the optical axis of the video camera 11 is swiveled in such a way that the optical axis 13 and the longitudinal axis 4 at least approximately intersect. As a result of this stepwise increase in the angle of convergence between the two axes, the optical axis 13 arrives in the same cross-sectional plane as that of the illuminated field 8, whereupon the distance is measured by the autofocus function of the video camera 11. After both the angle of inclination of the optical axis 13 to the longitudinal axis 4 and the distance between the illuminated field 8 and the video camera 11 are known, the trigonometric relationships are calculated by means of a preferably digital control unit, whereupon the optical axis 13 of the video camera 11 is adjusted in such a way that it intersects approximately the longitudinal axis 4 of the lamp housing 1 in the center of the illuminated field 8, with the result that the image recording process is free of parallax.

Thus, while there have been shown and described and pointed out fundamental novel features of the present invention as applied to a preferred embodiment thereof, it will be understood that various omissions and substitutions and changes in the form and details of the devices illustrated, and in their operation, may be made by those skilled in the art without departing from the spirit of the present invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

We claim:

1. A process for video recording a field illuminated by a lamp, comprising the step of:
    directing at least one light beam for illuminating the field from at least one light exit area of a lamp housing toward a predetermined housing axis;
    automatically adjusting the optical axis of a video camera, which is mounted on a bracket at a specified distance from the light exit with freedom to pivot the camera about a tilt axis, by a positioning element until the camera's optical axis intersects the at least one light beam in the area of the illuminated field; and
    determining a required adjustment distance by first panning the camera across an entire adjustment range and then pivoting the camera to a position of maximum image brightness.

2. A process according to claim 1, including driving the positioning element with signals from a control unit.

3. A process according to claim 2, including determining the distance to the illuminated field by a fine adjustment of camera focus aided by an autofocus function of the video camera, and sending signals from the control unit to the positioning element of the camera to compensate for parallax between the optical axis of the camera and the light beam.

4. A process according to claim 3, including using a zoom lens of the camera to enlarge the illuminated field to a maximum extent before activating the autofocus function of the video camera.

5. A process according to claim 1, including adjusting the video camera relative to the predetermined housing axis until the optical axis of the camera at least approximately intersects the predetermined housing axis.

6. A process according to claim 1, including pivoting the video camera in a stepwise manner.

7. A process according to claim 1, including iteratively correcting the alignment of the optical axis of the camera.

8. A lamp, comprising:
    at least one lamp housing;
    a light source arranged in the housing so that at least one light beam emerges in a direction of a predetermined axis to illuminate a field;
    a video camera arranged in the housing at a set distance away from one of an exit point of the light beam and the predetermined axis, the video camera having an optical axis and a positioning element operative to automatically shift the optical axis of the camera with respect to the at least one light beam or with respect to the predetermined axis of the lamp housing until the optical axis of the camera intersects the illuminated field;
    a control unit operative to drive the positioning element of the video camera, the control unit being responsive to driving signals which depend on orientation of the video camera with respect to the predetermined axis of the lamp housing or of the light beam; and
    an angle sensor operatively arranged to generate the driving signals, the sensor being operative to detect the orientation of the optical axis in space and the orientation of the lamp housing, of the predetermined axis, or of the light beam.

9. A lamp according to claim 8, and further comprising a photosensor to generator a driving signal for the control unit.

* * * * *

UNITED STATES PATENT AND TRADEMARK OFFICE
CERTIFICATE OF CORRECTION

PATENT NO. : 7,098,956 B2  Page 1 of 1
APPLICATION NO. : 10/017164
DATED : August 29, 2006
INVENTOR(S) : Joachim Keitel et al.

It is certified that error appears in the above-identified patent and that said Letters Patent is hereby corrected as shown below:

Title Page item 73

Please DELETE: Assignee Heraeus Med GmbH

Please INSERT: Assignee Maquet GmbH & Co. KG

Signed and Sealed this

Twenty-ninth Day of April, 2008

JON W. DUDAS
*Director of the United States Patent and Trademark Office*

UNITED STATES PATENT AND TRADEMARK OFFICE
CERTIFICATE OF CORRECTION

PATENT NO. : 7,098,956 B2 Page 1 of 1
APPLICATION NO. : 10/017164
DATED : August 29, 2006
INVENTOR(S) : Joachim Keitel et al.

It is certified that error appears in the above-identified patent and that said Letters Patent is hereby corrected as shown below:

On the title page item (73), DELETE: Assignee Heraeus Med GmbH and INSERT: Assignee Maquet GmbH & Co. KG Signed and Sealed this Thirteenth Day of May, 2008

JON W. DUDAS
*Director of the United States Patent and Trademark Office*